US009089656B2

(12) United States Patent
Plumptre

(10) Patent No.: US 9,089,656 B2
(45) Date of Patent: Jul. 28, 2015

(54) SPINDLE AND BEARING COMBINATION AND DRUG DELIVERY DEVICE

(75) Inventor: David Plumptre, Droitwich Spa (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 417 days.

(21) Appl. No.: 13/322,813

(22) PCT Filed: May 28, 2010

(86) PCT No.: PCT/EP2010/057488
§ 371 (c)(1),
(2), (4) Date: Mar. 15, 2012

(87) PCT Pub. No.: WO2010/139641
PCT Pub. Date: Dec. 9, 2010

(65) Prior Publication Data
US 2012/0165739 A1 Jun. 28, 2012

Related U.S. Application Data

(60) Provisional application No. 61/182,861, filed on Jun. 1, 2009.

(30) Foreign Application Priority Data

Jul. 10, 2009 (EP) ..................................... 09009046

(51) Int. Cl.
*A61M 5/50* (2006.01)
*A61M 5/315* (2006.01)

(52) U.S. Cl.
CPC ............ *A61M 5/5066* (2013.01); *A61M 5/3158* (2013.01); *A61M 5/31515* (2013.01); *A61M 5/31511* (2013.01); *A61M 5/5086* (2013.01); *Y10T 29/49826* (2015.01)

(58) Field of Classification Search
CPC .............. A61M 5/31586; A61M 5/24; A61M 5/31581; A61M 5/31535; A61M 5/31551; A61M 5/31515; A61M 5/14546; A61M 2005/2407; A61M 5/3148; A61M 2005/3112
USPC .................................. 604/229, 228, 224, 225
See application file for complete search history.

(56) References Cited

U.S. PATENT DOCUMENTS 4,677,980 A * 7/1987 Reilly et al. ................... 600/432
4,973,309 A * 11/1990 Sultan ........................... 604/110

(Continued)

FOREIGN PATENT DOCUMENTS

DE    102005060928 A1    6/2007
DE    102007026083 A1    11/2008

(Continued)

OTHER PUBLICATIONS

English Translation of the First Office Action for the Chinese Patent Application No. 201080030158.3, Mar. 26, 2013.

*Primary Examiner* — Bhisma Mehta
*Assistant Examiner* — William Frehe
(74) *Attorney, Agent, or Firm* — McDonnell Boehnen Hulbert & Berghoff LLP

(57) ABSTRACT

An improved spindle and bearing combination for a drug delivery device is provided that has a first connection between the spindle (1) and bearing (4) comprising a web (5) and a second connection that replaces the first connection when the web (5) is severed that allows the spindle (1) to rotate relative to the bearing (4).

8 Claims, 2 Drawing Sheets

(56) References Cited

U.S. PATENT DOCUMENTS

| | | | |
|---|---|---|---|
| 5,084,017 A * | 1/1992 | Maffetone | 604/110 |
| 5,085,638 A * | 2/1992 | Farbstein et al. | 604/110 |
| 5,423,757 A * | 6/1995 | Olovson et al. | 604/110 |
| 5,593,386 A * | 1/1997 | Helldin | 604/110 |
| 5,634,408 A * | 6/1997 | Jarkowski | 108/44 |
| 6,221,046 B1 * | 4/2001 | Burroughs et al. | 604/153 |
| 6,676,642 B2 * | 1/2004 | Beebe | 604/228 |
| 2008/0082055 A1 * | 4/2008 | Lloyd et al. | 604/218 |

FOREIGN PATENT DOCUMENTS

| | | |
|---|---|---|
| EP | 0937471 A2 | 8/1999 |
| WO | 9218180 A1 | 10/1992 |
| WO | 9639214 A1 | 12/1996 |
| WO | 2005018721 A1 | 3/2005 |
| WO | 2005123159 A2 | 12/2005 |

* cited by examiner

SPINDLE AND BEARING COMBINATION AND DRUG DELIVERY DEVICE

CROSS REFERENCE TO RELATED APPLICATIONS

The present application is a 35 U.S.C. 371 National Application of PCT/EP2010/057488 filed May 28, 2010, which claims priority to U.S. Provisional Patent Application No. 61/182,861 filed Jun. 1, 2009 and European Patent Application No. 09009046.5 filed Jul. 10, 2009, the entire contents of which are incorporated entirely herein by reference.

THE TECHNICAL FIELD OF THE INVENTION

The present invention relates to a drug delivery device containing an improved spindle used to expel a medicament from a container. The invention further concerns a drug delivery device comprising such spindle and a method of fabricating a drug delivery device.

DESCRIPTION OF RELATED ART

Most drug delivery devices use a spindle to advance an elastic (rubber) piston positioned within one end of a container of medicament to cause the medicament to exit the opposite end of the container. In some delivery devices it is necessary to rotate the spindle during dose delivery relative to the rubber piston. To accomplish this movement and to reduce frictional losses a bearing plate or disk is positioned at the distal end of the spindle abutting the proximal face of the non-rotatable rubber piston. This bearing plate is typically connected with a universal joint type connection, i.e. one where the spindle can freely rotate and articulate about the center point of the top surface of the plate. As the spindle is rotated and moved in an axial direction the bearing is prevented from rotating because of its engagement with the non-rotatable piston causing both the bearing plate and piston to also move in the axial direction imparting a pressure to the medicament causing it to be expelled from the distal end of the container. Prior to the invention the spindle and bearing were necessarily manufactured as two separate parts, which were then snapped together before being assembled into the drug delivery device.

A common example of a drug delivery device is an injection device that contains a multi-dose cartridge. A more specific example would be a pen-type injection device containing a cartridge of insulin that is designed for repeated injections by persons without formal medical training occurs, i.e., patients. This is increasingly common amongst those having diabetes where self-treatment enables such persons to conduct effective management of their diabetes.

Maintaining of drug delivery devices at reasonable prices or reducing the cost is a priority for manufacturers of such devices.

It is therefore an object of the present invention to provide an improved drug delivery device which can be manufactured with reduced costs and to specify a cost saving method of fabricating a drug delivery device.

SUMMARY OF THE INVENTION

The above object is solved by an improved spindle and bearing combination for use in a drug delivery device comprising a rotatable spindle having a distal end and a disk-shaped bearing attached to the distal end of the spindle through a first connection comprising a web that fixedly attaches the bearing to the spindle to prevent independent movement of the bearing relative to the spindle. This first connection is replaced by a second connection which is created when the web is severed and the web is disconnected from the bearing.

The advantage of the inventive solution of the improved spindle and bearing combination is that the number of parts in the device is minimized. Further, the assembling steps needed to fabricate the device are improved. The invention therefore achieves both of these cost saving features by providing a spindle and bearing combination that can be integrally manufactured (for example moulded) and assembled as a unitary piece. Further, the combination has a first connection between the spindle and disk-shaped bearing that changes to a second connection before a first dose of medicament is delivered to the user making the usage safe. Preferably, the replacement of the first connection forming the second connection is accomplished during the assembly of the device before it leaves the factory. The invention is of greater value when the device is designed as a disposable device rather than reusable device because a disposable device must be as inexpensive as possible to manufacture and easy to dispose of (preferably being suitable for recycling). To meet these requirements the number of parts required for assembly of the device and the number of material types the device is made from need to be kept to a minimum. These and other advantages will become evident from the following more detailed description of the invention.

In a preferred embodiment the spindle has at least one helical groove positioned longitudinally along the spindle. In a preferred embodiment the second connection is a rotating joint connection, i.e. one where the spindle can freely rotate.

Shearing of the web can occur by applying an axial force to the spindle and bearing combination after the combination has been assembled into the drug delivery device. Alternatively, a rotational force can be applied to the bearing plate to shear the web. Either force can be applied by the manufacturer of the device or by the user immediately before or during the delivery of a first dose of medicament.

The above objection is further solved by a drug delivery device comprising the spindle and bearing combination described above.

The term "drug delivery device" according to instant invention shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The terms "drug" or "medicinal product" or "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The term "engaged" according to instant invention shall particularly mean the interlocking of two or more components of the drive mechanism/drug delivery device, e.g. a spline, thread, or meshed teeth connection, preferably the interlocking of helical grooves or threads of components ("rotationally engaged" or "threadedly engaged").

The term "spindle" according to instant invention shall mean a component adapted to operate through/within the housing, designed to translate axial movement through/within the drug delivery device, preferably from a driver to the piston, for the purpose of discharging/dispensing an injectable product. The spindle may be flexible or not. It may be a simple rod, a lead-screw, a rack and pinion system, a worm gear system, or the like. The spindle shall further mean a component having a circular or non-circular cross-section. It may be made of any suitable material known by a person skilled in the art. The spindle and the bearing are usually part of the injection device of the drug delivery device. The injection device is responsible for expelling the medical product out of the drug delivery device.

In a preferred embodiment, the spindle comprises at least one, more preferably two, external and/or internal helical grooves or threads. In another preferred embodiment of the spindle, a first helical groove is located at a first end and a second helical groove is located at a second end of the spindle, whereby the said groves may have the same or, preferably, opposite dispositions and may overlap each other. In another preferred embodiment the spindle invention comprises grooves having the same leads at the first and the second end.

In yet another preferred embodiment of instant invention the lead of the first helical groove of the spindle shall be greater than the lead of the second helical groove. More preferred, the ratio of the leads of the helical grooves of the said first and the second helical grooves 1:1.01 to 1:20, even more preferred 1:1.1 to 1:10. Preferably, one of the said grooves is designed to engage a driver to impart either rotation, axial or a combination of rotational and axial movement to the spindle.

The term "first end" according to instant invention shall mean the proximal end. The proximal end of the device or a component of the device shall mean the end, which is closest to the dispensing end of the device.

The term "second end" according to instant invention shall mean the distal end. The distal end of the device or a component of the device shall mean the end, which is furthest away from the dispensing end of the device.

The above object is further solved by a method of fabricating a drug delivery device comprising the steps of
providing a unitary part of a spindle and bearing combination comprising,
a spindle having a distal end and preferably at least one helical groove positioned longitudinally along the spindle; and
a disk-shaped bearing having a first connection comprising a web that fixedly attaches the bearing to the spindle and preventing independent movement of the bearing relative to the spindle;
assembling the unitary part into a housing of the drug delivery device; and
severing the web and disconnecting it from the bearing to form a second connection of the bearing to the spindle replacing the first connection, preferably comprising a joint that allows the spindle to rotate relative to the bearing.

BRIEF DESCRIPTION OF THE DRAWINGS

Without any limitation, the instant invention will be explained in greater detail below in connection with a preferred embodiment and with reference to the drawings in which.

DETAILED DESCRIPTION OF THE EMBODIMENTS

Figure 1:
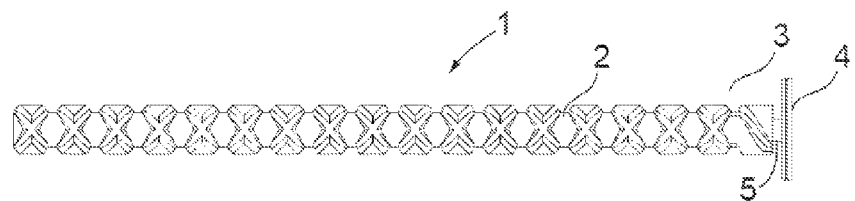
FIG. 1 shows a side view of the inventive spindle bearing combination where the spindle is connected to disk-shaped bearing by a web such that the bearing cannot move independently of the spindle.
Figure 3:
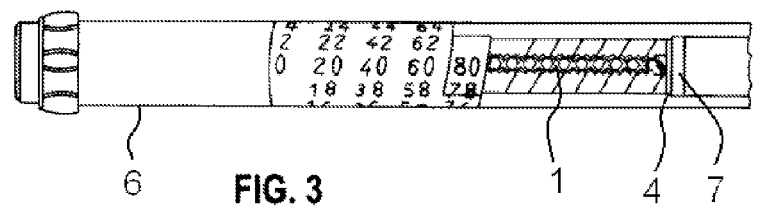
FIG. 3 shows a side and partly cross-sectional view of an example of an inventive drug delivery device where the invention can be used.

Referring first to FIG. 1 there is shown a spindle 1 that has two overlapping helical grooves 2 running longitudinally along the spindle having attached to its distal end 3 a disk-shaped bearing 4. Although two helical grooves are depicted a single groove or no groove could also be used. Preferably the combination of the spindle and bearing is fabricated as a single moulded part of a polymer material, such as plastic, however, a metal or combination of different materials could be used provided that the material of construction of web 5 can be broken or sheared upon application of a rotational or axial force. The strength or robustness of the web need only be sufficient to allow for the assembly of the combination of the spindle and bearing as a part of the injection device in a drug delivery device 6 like the representative device shown in FIG. 3 where bearing 4 is abutting piston 7 moving in a cartridge in order to expel medication.

Figure 4:
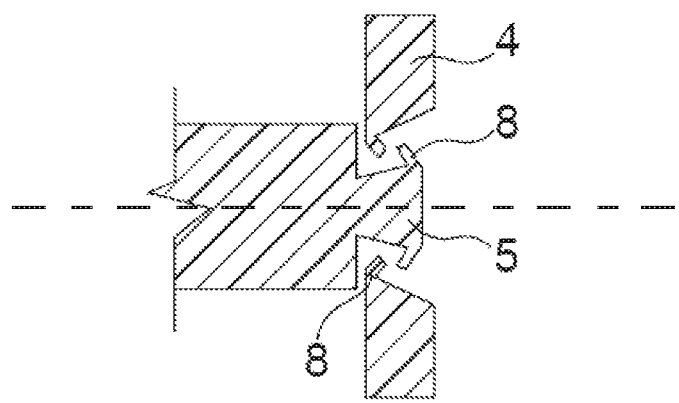
FIG. 4 shows a close up cross-sectional view of the second connection after the web of FIG. 1 is sheared.

Once the combination spindle and bearing of the invention is assembled into the delivery device 6, the manufacturer or the user will impart a rotational or axial force to the spindle 1. This will cause the web 5 of the first connection to break allowing the spindle 1 to rotate relative to the stationary bearing 4 thus forming a second rotating joint connection. The web 5 can be of any shape or design as long as it is strong enough to hold the bearing 4 to the distal end 3 of the spindle 1 during assembly of the drug delivery device 6 and is weak enough to shear when a rotational or axial force is applied to the spindle 1. One preferred web design is where the thickness of the plastic is reduced in a circumferential line (not shown in the Figures) at the point where the face of the bearing 4 and the web 5 meet. A rotational or axial force applied to the spindle 1 will be transferred to this circumferential line of thin plastic and will shear the web 1 from the proximal face of the bearing 4. The shape of the distal end of the spindle 1 and the proximal face of the bearing 4 is configured to allow the formation of a rotational connection between the separate parts after the web shear is broken. In a preferred configuration the web 5 is designed such that upon shearing the respective pieces of the web 5 form a type of snap fit or snap lock that holds the bearing 4 to the spindle 1, yet allows the spindle 1 to rotate with respect to the bearing 4. A most preferred design is where no pieces are broken off from the spindle 1 or the bearing 4 that could fall into the device and cause a malfunction. This is illustrated in FIG. 4 where the resulting web shears 8 remain attached to the spindle 1 and bearing 4. Because the web 5 deforms and stretches during the breaking process, the result is two cooperating pieces 8 that work together in order to retain the bearing 4 on the spindle 1.

Figure 2:
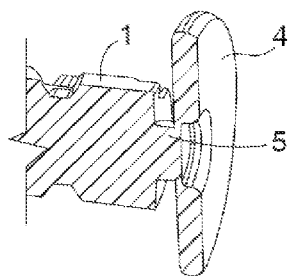
FIG. 2 shows a close up cross-sectional view of the web and a part of the spindle bearing combination of FIG. 1.

Although the web 5 that is shown in FIGS. 1 and 2 is a cylindrical element, it could also take other forms provided that the bearing 4 is free to rotate in the second connection and adequately secured in the first connection.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The means, materials, and steps for carrying out various disclosed functions may take a variety of alternative forms without departing from the invention. Thus, the expressions "means to . . . " and "means for . . . ", or any method step language as may be found in the specification above or the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation within the terms of the following claims.

The invention claimed is:

1. A spindle and bearing combination for use in a drug delivery device comprising a cartridge, the combination comprising,
    a spindle having a distal end; and
    a disk-shaped bearing adapted to abut a piston in the cartridge, the bearing comprising a first connection and a second connection to the distal end of the spindle, and wherein the bearing and spindle are formed as one unitary part,
    where the first connection comprises a web that fixedly attaches the bearing to the spindle to prevent independent movement of the bearing relative to the spindle and
    where the second connection is created and replaces the first connection when the web is sheared and disconnected from the bearing,
    and wherein the second connection comprises a joint that allows the spindle to rotate relative to the bearing.

2. A drug delivery device comprising the spindle and bearing combination claim 1 wherein the spindle and the bearing are assembled as part of an injection device when the first connection remains intact.

3. The drug delivery device of claim 2 wherein the spindle and bearing are connected with the second connection during delivery of a first dose with the injection device.

4. The drug delivery device of claim 2 wherein the spindle and bearing combination are assembled as part of the injection device and the first connection is modified to the second connection during the assembly of the injection device.

5. The drug delivery device of claim 1 comprising a cartridge of medication.

6. The spindle and bearing combination of claim 1 wherein the second connection prevents accidental separation of the bearing from the spindle.

7. The spindle and bearing combination of claim 1 wherein the spindle has at least one helical groove positioned longitudinally along the spindle.

8. A method of fabricating a drug delivery device comprising the steps of
    a. providing a spindle having a distal end and a disk-shaped bearing adapted to abut a piston in the cartridge, the bearing comprising a first connection and a second connection to the distal end of the spindle, and wherein the bearing and spindle are formed as one unitary part, where the first connection comprises a web that fixedly attaches the bearing to the spindle to prevent independent movement of the bearing relative to the spindle;
    b. assembling the unitary part into a housing of the drug delivery device; and
    c. severing the web and disconnecting it from the bearing to form the second connection of the bearing to the spindle replacing the first connection, comprising a joint that allows the spindle to rotate relative to the bearing.

* * * * *